(12) United States Patent
Heigl et al.

(10) Patent No.: US 8,068,658 B2
(45) Date of Patent: Nov. 29, 2011

(54) EVALUATION METHOD FOR TWO-DIMENSIONAL FLUOROSCOPY IMAGES OF AN EXAMINATION OBJECT WITH TIME-CODED DISPLAY OF THREE-DIMENSIONAL RECONSTRUCTIONS

(75) Inventors: Benno Heigl, Coburg (DE); Klaus Klingenbeck-Regn, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 408 days.

(21) Appl. No.: 12/431,388

(22) Filed: Apr. 28, 2009

(65) Prior Publication Data

US 2009/0279766 A1 Nov. 12, 2009

(30) Foreign Application Priority Data

May 9, 2008 (DE) .......................... 10 2008 023 053

(51) Int. Cl.
*G06K 9/00* (2006.01)
*A61B 5/05* (2006.01)
*H05G 1/64* (2006.01)

(52) U.S. Cl. .......... 382/132; 382/128; 382/154; 378/62; 600/407; 600/411; 600/476

(58) Field of Classification Search .................. 382/154, 382/128–132; 378/62, 4, 8, 21, 23; 600/523, 600/410, 411, 427, 407, 476
See application file for complete search history.

(56) References Cited

U.S. PATENT DOCUMENTS

| | | | | |
|---|---|---|---|---|
| 6,911,996 | B1* | 6/2005 | Takemoto | 348/61 |
| 7,376,254 | B2* | 5/2008 | Barth | 382/131 |
| 7,961,924 | B2* | 6/2011 | Viswanathan | 382/128 |
| 2005/0020902 | A1* | 1/2005 | Janes | 600/407 |
| 2007/0003016 | A1* | 1/2007 | Brunner et al. | 378/98.12 |
| 2007/0232886 | A1* | 10/2007 | Camus et al. | 600/407 |
| 2008/0064974 | A1* | 3/2008 | Boese et al. | 600/523 |
| 2008/0123928 | A1* | 5/2008 | Harer et al. | 382/131 |
| 2008/0137924 | A1* | 6/2008 | Boese et al. | 382/128 |
| 2008/0317305 | A1* | 12/2008 | Cover et al. | 382/128 |
| 2009/0297005 | A1* | 12/2009 | Heigl | 382/130 |
| 2010/0128955 | A1* | 5/2010 | Walimbe et al. | 382/132 |
| 2010/0310141 | A1* | 12/2010 | Wilson | 382/131 |

FOREIGN PATENT DOCUMENTS

DE 10000185 A1 7/2001
DE 10100572 A1 7/2002

* cited by examiner

*Primary Examiner* — Hoa Pham

(57) ABSTRACT

A computer receives a plurality of two-dimensional fluoroscopy images of an examination object, capture time points and projection parameters and combines the images into image groups. Each image group contains all the images, the capture time point of which is between a minimum and a maximum time point specific to the respective image group. When the image groups are sorted by ascending minimum time points, the corresponding maximum time points form a strictly monotonously ascending order. The respective minimum and maximum time points are determined so that the computer reconstructs a three-dimensional object reconstruction of the examination object based on the images assigned to the respective image group. A respective two-dimensional reconstruction display is determined by the respective three-dimensional object reconstruction and outputted to a user in a coding specific to the respective image group by a display device.

11 Claims, 10 Drawing Sheets

EVALUATION METHOD FOR TWO-DIMENSIONAL FLUOROSCOPY IMAGES OF AN EXAMINATION OBJECT WITH TIME-CODED DISPLAY OF THREE-DIMENSIONAL RECONSTRUCTIONS

CROSS REFERENCE TO RELATED APPLICATIONS

This application claims priority of German application No. 10 2008 023 053.7 filed May 9, 2008, which is incorporated by reference herein in its entirety.

FIELD OF THE INVENTION

The present invention relates to an evaluation method for a plurality of two-dimensional fluoroscopy images of an examination object.

BACKGROUND OF THE INVENTION

The subject matter described above is generally known. It is used in particular to determine and display the blood flow in vascular systems. To this end a contrast agent is injected into the bloodstream and its propagation is captured and displayed. The displayed propagation of the contrast agent enables the user (generally a physician) to make an appropriate diagnosis.

The evaluation method of the prior art already operates well but is capable of improvement.

SUMMARY OF THE INVENTION

The object of the present invention is to create possibilities that allow improved and simpler diagnosis by the physician. In particular it should be possible to capture temporal assignment easily and intuitively.

The object is achieved for the evaluation method, based on an evaluation method of the type described above, in such a manner that the computer outputs each two-dimensional reconstruction display in a coding specific to the respective image group. For the computer program the object is achieved in that it is embodied correspondingly, so that it brings about the execution of such a further developed evaluation method. The same applies to the data medium and the computer.

Advantageous embodiments of the inventive evaluation method are described in the claims. The preferred embodiments also apply correspondingly to the computer program, the data medium and the computer.

The object is achieved by the evaluation method for a plurality of two-dimensional fluoroscopy images of an examination object, in which a computer receives the fluoroscopy images,
in which a capture time point at which the respective fluoroscopy image was captured and projection parameters subject to which the respective fluoroscopy image was captured are assigned to each fluoroscopy image,
in which the computer combines the fluoroscopy images into image groups in such a manner that
the respective image group contains all the fluoroscopy images, the capture time point of which is between a minimum time point specific to the respective image group and a maximum time point specific to the respective image group and
when the image groups are sorted by ascending minimum time points, the corresponding maximum time points form a strictly monotonously ascending order,
in which the respective minimum time point and the respective maximum time point for each image group are defined in such a manner that the fluoroscopy images assigned to the respective image group can be used to determine a three-dimensional object reconstruction of the examination object,
in which the computer determines the respective object reconstruction for each image group based on the fluoroscopy images assigned to the respective image group,
in which the computer uses the respective three-dimensional object reconstruction to determine a respective two-dimensional reconstruction display,
in which the computer outputs the two-dimensional reconstruction displays to a user by way of a display device.

It is possible for the respective coding to be a color assigned to the respective image group. For example the temporally first reconstruction display can be coded red, the temporally second two-dimensional reconstruction display yellow, the temporally third reconstruction display green etc. Alternatively or additionally the respective coding can be a fill structure assigned to the respective image group. For example the temporally first reconstruction display can be display with a full structure, the temporally second reconstruction display checkered, the temporally third reconstruction display hatched, the temporally fourth reconstruction display dotted, etc.

It is possible for the computer to output the reconstruction displays simultaneously. Alternatively it is possible for the computer to output the reconstruction displays as a temporal sequence.

If the reconstruction displays are output as a temporal sequence, it is possible for the computer to display the reconstruction displays in full. In one preferred embodiment of the present invention however the computer only outputs the part of each reconstruction display that corresponds to none of the temporally preceding reconstruction displays. This last procedure can also be realized even if the computer outputs the reconstruction displays simultaneously. In this process, when outputting the respective part of the respective reconstruction display the computer can optionally also output the corresponding parts of the temporally preceding reconstruction displays.

It is possible for the examination object to be static; in other words it does not move when the fluoroscopy images are being captured. One example of such a static examination object is the human brain and the blood vessel system, which supplies the brain with blood. Alternatively the examination object can be a moving examination object. For example the person can move their head. There can also be respiration-induced or pulse-induced motion when capturing the lungs or abdomen.

It is possible to capture information about an inherent motion of the examination object while the fluoroscopy images are being captured and to supply this to the computer. In this instance the computer receives this information in addition to the fluoroscopy images. The computer is then able to carry out registration of the fluoroscopy images corresponding to the inherent motion of the examination object before determining the object reconstructions. Alternatively or additionally the computer can also carry out registration of the fluoroscopy images corresponding to the inherent motion of the examination object after determining the object reconstructions.

Registration methods for registering the two-dimensional fluoroscopy images relative to one another—and also automatic registration methods—are known per se from the prior art. They are as such not the subject matter of the present invention. The same applies to registration methods used to register the three-dimensional object reconstructions relative to one another in some instances.

It is possible for the computer to determine the minimum time points and maximum time points of the image groups individually. In particular where there is continuous movement of the recording arrangement used to capture the fluoroscopy images it is however possible and also advantageous, if the computer determines the minimum time points and maximum time points of the image groups in such a manner that directly consecutive minimum time points have a uniform temporal setpoint interval for all the image groups and for each image group the difference between the respective maximum time point and the respective minimum time point is equal to a uniform setpoint time period for all the image groups. Continuous movement of the recording arrangement is in particular a continuous rotation of the recording arrangement of a CT system. C-arm systems can also bring this about in some instances.

The temporal setpoint interval is generally at least as long as half the setpoint time period. It is preferably even as long as the setpoint time period.

It is possible for the temporal setpoint interval to be permanently predetermined for the computer or to be determined by the computer based on otherwise predetermined variables. Alternatively the computer can receive the temporal setpoint interval from the user.

BRIEF DESCRIPTION OF THE DRAWINGS

Further advantages and details will emerge from the description which follows of exemplary embodiments in conjunction with the drawings of basic diagrams, in which.

DETAILED DESCRIPTION OF THE INVENTION

Figure 1:
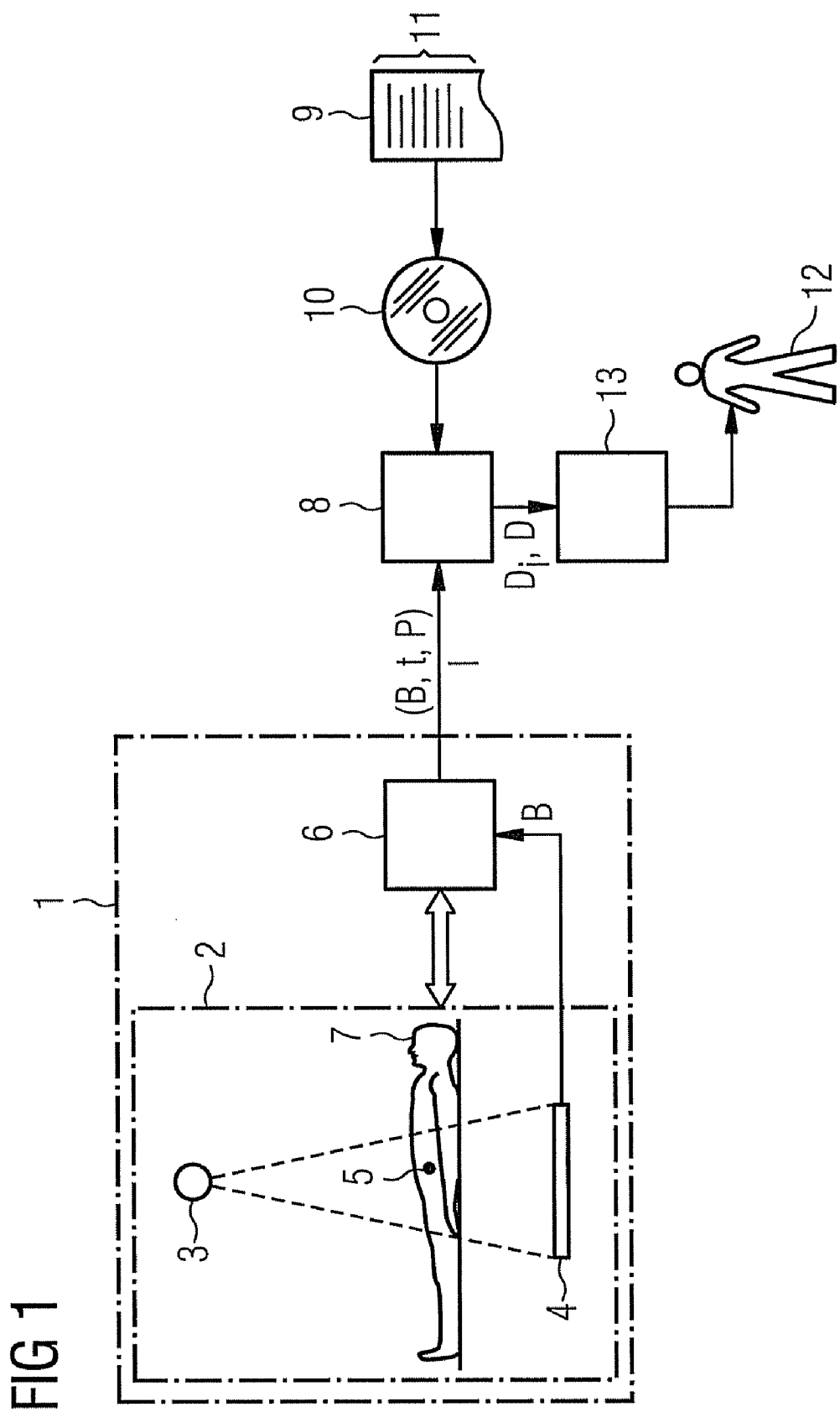
FIG. 1 shows an x-ray system and an evaluation arrangement.

According to FIG. 1 an x-ray source 1 has a recording arrangement 2. The recording arrangement 2 comprises an x-ray source 3 and a flat panel detector 4. The x-ray source 3 and flat panel detector 4 can be moved together. Generally they can be pivoted about a common pivot axis 5, as shown by corresponding arrows in FIG. 1. Displacement of the x-ray source 3 and flat panel detector 4 is generally coordinated in this process, so that the pivot axis 5 is disposed between the x-ray source 3 and the flat panel detector 4 at any time point.

The x-ray system 1 is controlled by a control facility 6. Further to corresponding activation by the control facility 6 the flat panel detector 4 captures a two-dimensional fluoroscopy image B of an examination object 7 disposed in the region of the pivot axis 5, for example the brain of a human 7, from a start time point at capture time points t respectively. The start time point here is selected as required. Generally it is defined in such a manner that it coincides with the start of the introduction of a contrast agent into the part of the blood vessel system of the examination object 7 under consideration.

The control facility 6 transmits the captured fluoroscopy images B to a computer 8. Together with the fluoroscopy images B the control facility 6 transmits to the computer 8 the associated capture time point t for every fluoroscopy image B as well as the projection parameters P, subject to which the respective fluoroscopy image B was captured by means of the recording arrangement 2.

The computer 8 can be a standard computer. The computer 8 is programmed using a computer program 9. The computer program 9 can be stored in machine-readable form on a data medium 10 for example and be supplied to the computer 8 by way of the data medium 10. A CD-ROM is shown as the data medium 10 in FIG. 1 purely by way of example. The data medium 10 could however be configured differently, for example as a USB memory stick or as an SD memory card.

The computer program 9 has machine code 11. The machine code 11 can be executed directly by the computer 8. Execution of the machine code 11—which naturally takes place during operation of the computer 8—causes the computer 8 to execute an evaluation method, which is described in more detail below in conjunction with FIG. 2.

Figure 2:
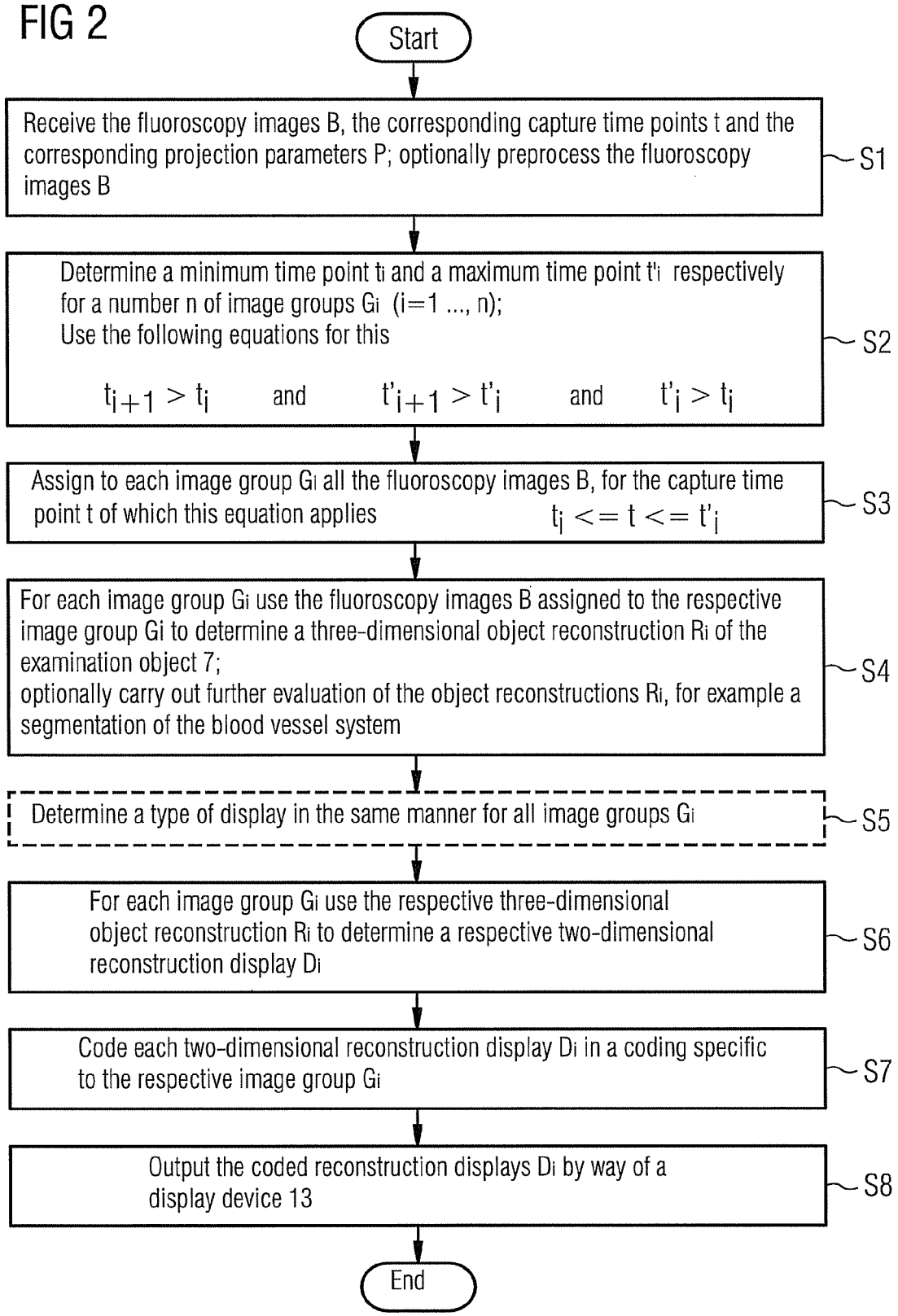
FIG. 2 to 4 show flow diagrams.

According to FIG. 2 in a step S1 the computer 8 receives the fluoroscopy images B. Each fluoroscopy image B is hereby assigned the corresponding capture time point t and the corresponding projection parameters P. The number of received fluoroscopy images B is generally very large. Generally significantly more than 100 fluoroscopy images B are received, for example 200, 300, 450 or yet more fluoroscopy images B. In the context of step S1 the computer 8 can also preprocess the individual fluoroscopy images B, for example using DSA (=digital subtraction angiography) or contrast amplification.

In a step S2 the computer 8 determines a minimum time point $t_i$ and a maximum time point $t'_i$ respectively for a number n of image groups $G_i$ (i=1 . . . , n). In this process the following equations apply irrespective of the value of the index i $$t_{i+1} > t_i$$

$$t'_{i+1} > t'_i \text{ and}$$

$$t'_i > t_i.$$

The difference between directly consecutive minimum time points (i.e. $t_{i+1} - t_i$) is referred to below as the group interval. The group interval can be the same for all image groups $G_i$. However this is not necessarily the case.

Similarly the difference between the maximum time point $t'_i$ and minimum time point $t_i$ for each image group $G_i$ is referred to below as the group time period. The group time period can—like the group time interval—be the same for all image groups $G_i$. However this is also not necessarily the case.

In a step S3 the computer 8 forms the image groups $G_i$. Each image group $G_i$ here comprises all the fluoroscopy images B, the capture time point t of which is between the minimum time point $t_i$ and the maximum time point $t'_i$ of the respective image group $G_i$.

The minimum time points $t_i$ and the maximum time points $t'_i$ are defined in such a manner for all the image groups $G_i$ that a respective three-dimensional object reconstruction $R_i$ of the examination object 7 can be determined for each image group $G_i$ based on the fluoroscopy images B assigned to the respective image group $G_i$. The computer 8 carries out this determination in a step S4. If necessary in step S4 the computer 8 can carry out a further evaluation of the object reconstructions $R_i$, for example a segmentation of the blood vessel system of the examination object 7, to the extent that contrast agent flows through it in the context of the object reconstruction $R_i$ considered in each instance.

In a step S5 the computer 8 determines a type of display in the same manner for all object reconstructions $R_i$. For example the computer 8 can determine whether there should be a parallel projection, a perspective projection or a sectional display. Further display parameters (viewing direction, viewing angle, etc.) can also be determined in some instances.

Step S5 is only optional. It is therefore shown with a broken line in FIG. 2. If it is not present, the type of display can be permanently predetermined for example.

Step S5 can—if present—operate fully automatically. Alternatively the cooperation of a user 12 may be required. The cooperation of the user 12 can optionally be of an interactive nature, it then being possible for the input of the user 12 to be changed at any time.

In a step S6 the computer 8 uses the respective three-dimensional object reconstruction $R_i$ for the respective image group $G_i$ to determine a respective two-dimensional reconstruction display $D_i$. The respective reconstruction display $D_i$ is determined here taking into account the type of display defined in step S5 (or the otherwise known type of display).

In a step S7 the computer 8 codes each two-dimensional reconstruction display $D_i$ in a coding. The coding here is specific to the respective image group $G_i$. The respective coding can be a color assigned to the respective image group $G_i$ for example. Alternatively or additionally the respective coding can be a fill structure assigned to the respective image group $G_i$. Both procedures are described in more detail below in conjunction with FIG. 3 to 6.

In a step S8 the computer 8 outputs the coded reconstruction displays $D_i$ to the user 12 by way of a display device 13.

Figure 3:
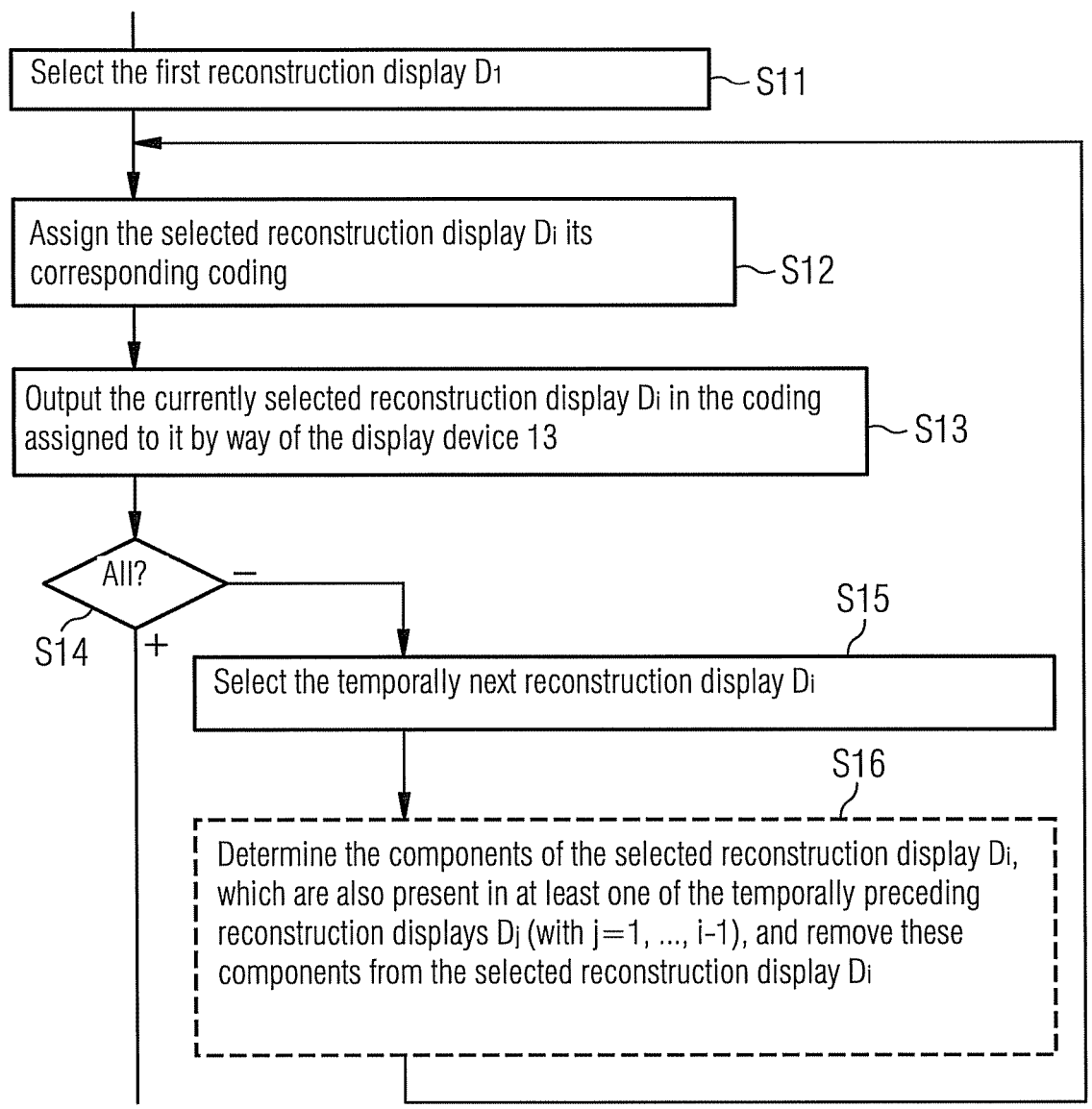

FIG. 3 shows a possible implementation of steps S7 and S8 in FIG. 2.

According to FIG. 3 in a step S11 the computer 8 selects the first reconstruction display $D_1$. In a step S12 the computer 8 assigns the first reconstruction display $D_1$ its corresponding coding. In a step S13 the computer 8 outputs the currently selected reconstruction display $D_i$ to the user 12 in the coding assigned to it by way of the display device 13.

In a step S14 the computer 8 checks whether it has already executed step S13 for all the reconstruction displays $D_i$. If not, the computer 8 passes on to a step S15. Otherwise the method in FIG. 3 is terminated.

In step S15 the computer 8 selects the temporally next reconstruction display $D_i$. The computer 8 then goes back to step S12.

The procedure in FIG. 3 results in the computer 8 outputting the individual reconstruction displays $D_i$ one after the other, in other words as a temporal sequence, to the user 12 by way of the display device 13. Each reconstruction display $D_i$ is hereby output in its corresponding coding.

As described to date, with the procedure in FIG. 3 the respective reconstruction display $D_i$ is output in its entirety. Optionally however it is possible to assign a further step S16 after step S15. Step S16 is only shown with a broken line in FIG. 3, because it is optional.

If step S16 is present, in step S16 the computer 8 determines the components of the selected reconstruction display $D_i$, which are also present in at least one of the temporally preceding reconstruction displays $D_j$ (with j=1, . . . , i−1). As part of step S16 the computer 8 removes these components from the selected reconstruction display $D_i$. This modification means that for each reconstruction display $D_i$ respectively the computer 8 only outputs the part which corresponds to none of the temporally preceding reconstruction displays $D_j$.

Figure 4:
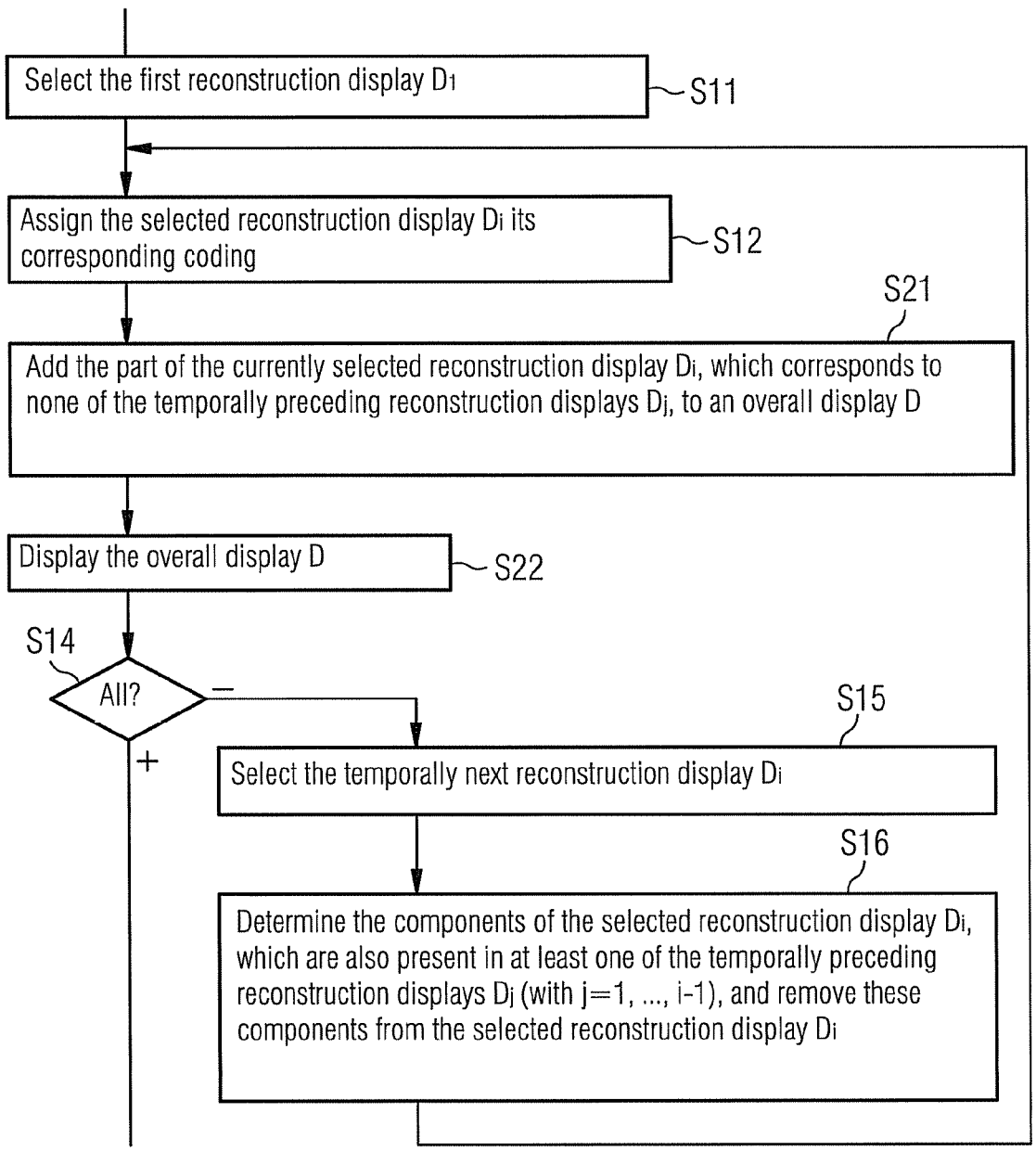

FIG. 4 shows a similar procedure to the procedure described just above in conjunction with FIG. 3 and the optional step S16. The procedure in FIG. 4 essentially differs from the last described procedure in FIG. 3 in that step S13 in FIG. 3 is replaced by steps S21 and S22. In step S21 the computer 8 adds the part of the currently selected reconstruction display $D_i$, which corresponds to none of the temporally preceding reconstruction displays $D_j$, to an overall display D. The overall display D is displayed in step S22.

Figure 5:
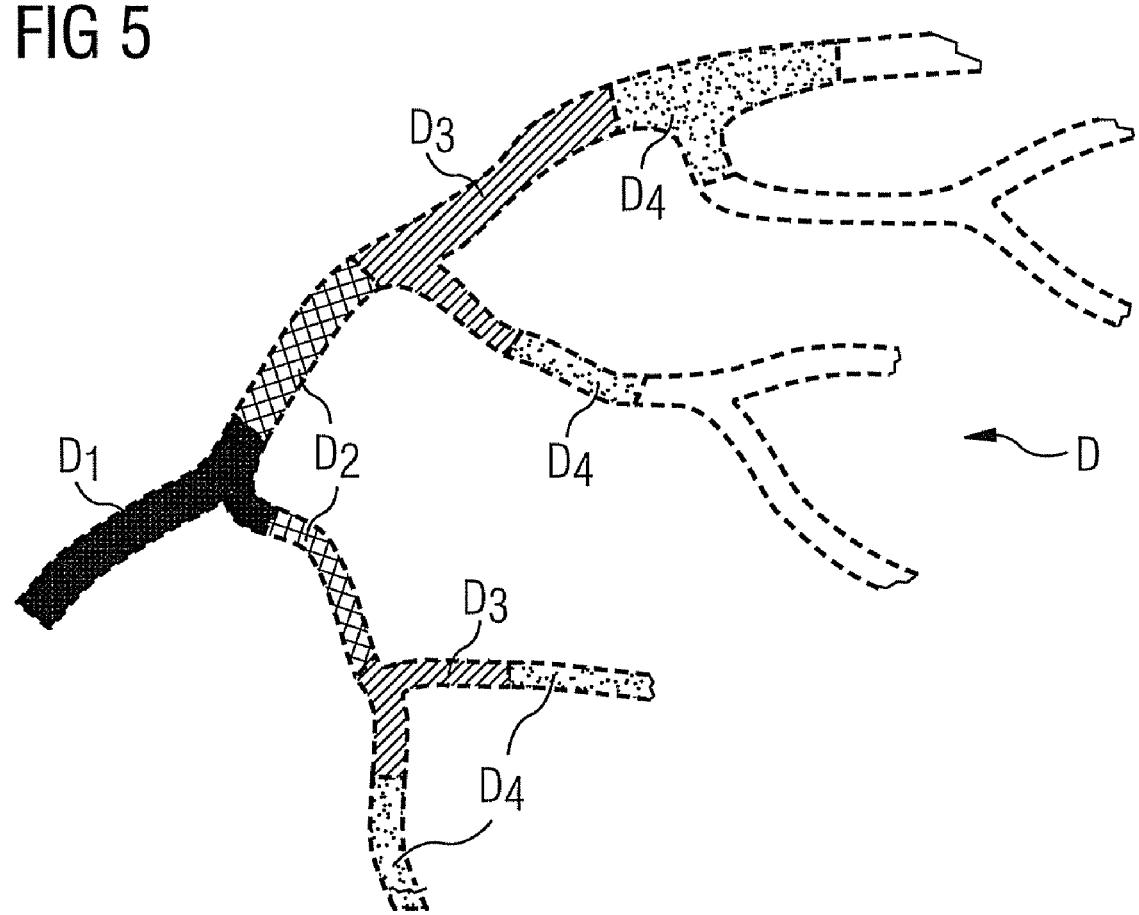
FIG. 5 shows an overall display.

The procedure according to FIG. 4 means that during the first iteration the first reconstruction display $D_1$ is output by way of the display device 13 in the coding assigned to the first reconstruction display $D_1$, during the second iteration the part of the second reconstruction display $D_2$ in the coding assigned to the second reconstruction display $D_2$, which was not already displayed in the context of the first reconstruction display $D_1$, is also displayed, etc. During the last iteration each part of the reconstruction displays $D_i$ is displayed in the coding in which it first comes up. The progression of the propagation of the contrast agent is thus visualized. FIG. 5 shows this procedure.

As mentioned above, the coding can be a color assigned to the respective image group $G_i$. For example the first reconstruction display $D_1$ can be displayed in red, the second reconstruction display $D_2$ in orange, the third reconstruction display $D_3$ in yellow, etc. It is likewise possible to assign the color red for example to the first reconstruction display $D_1$ and the color yellow to the last reconstruction display $D_n$. Transition colors from red to yellow are then assigned gradually to the other reconstruction displays $D_2$ to $D_{n-1}$. It is pointed out here for the sake of completeness only that the specified colors are purely exemplary.

As an alternative or in addition to the assignment of colors, a respective fill structure can be assigned to the respective reconstruction displays $D_i$. For example the first reconstruction display $D_1$ can be displayed completely filled in, the second reconstruction display $D_2$ with large checkering, the third reconstruction display $D_3$ with fine checkering, the fourth reconstruction display $D_4$ hatched, the hatching running from bottom left to top right, etc. It is likewise possible for example to assign a relatively large number of fill elements to the first reconstruction display $D_1$, so that a background is 80% or more covered, and to assign a fill structure, with which only a relatively small proportion of the background is filled, for example 20% or less, to the last reconstruction display $D_n$. In this instance the other reconstruction displays $D_2$ to $D_{n-1}$ can show a gradual reduction in the degree of cover from (purely by way of example) 90% to 10%.

Figure 6:
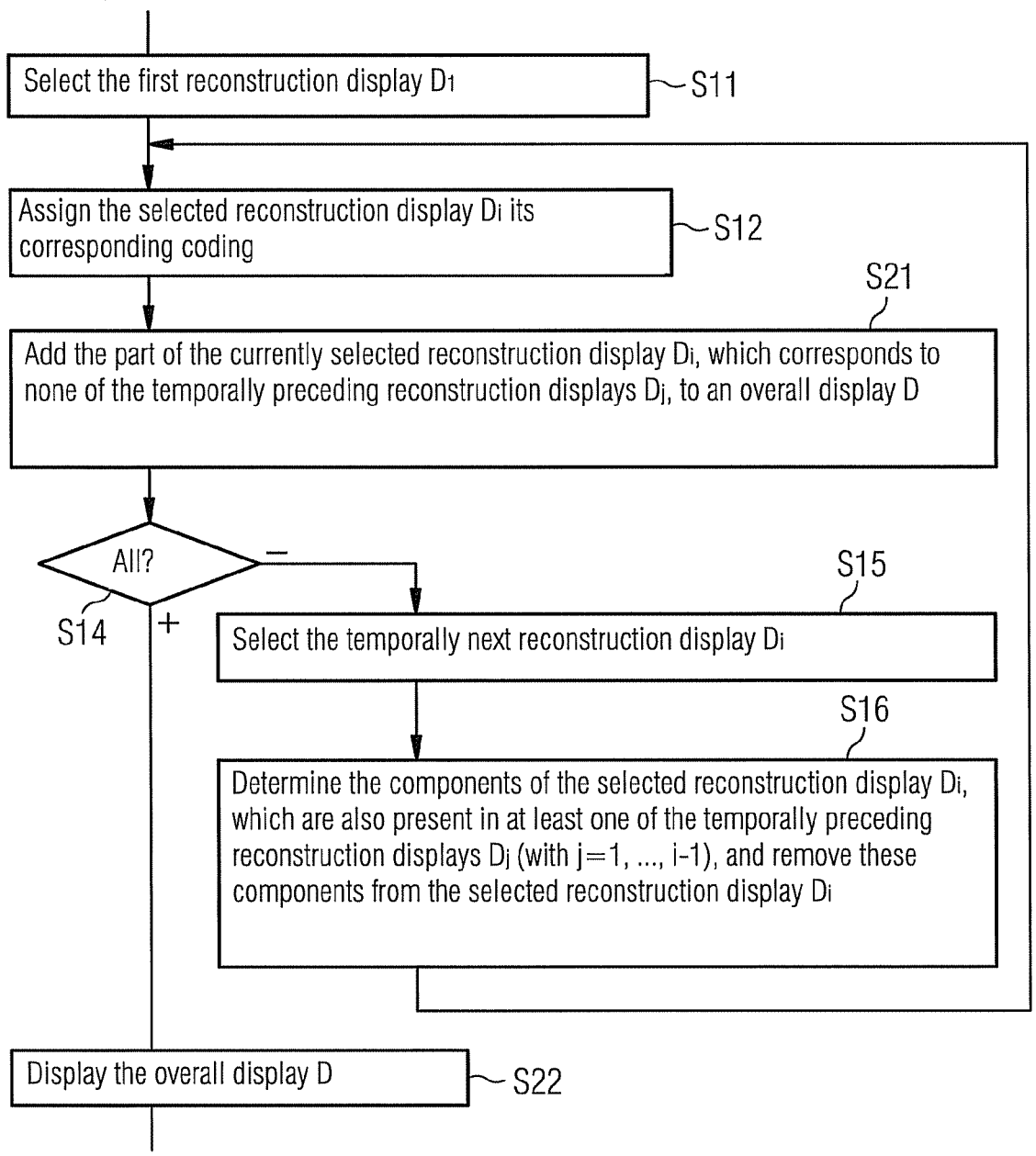
FIG. 6 shows a flow diagram.

FIG. 6 shows a slight modification of the procedure in FIG. 4. The difference is that step S22 is not executed in the context of the loop between steps S12 and S16, but only after leaving the loop, in other words if the check in step S14 is positive. This modification means that in the context of the overall display D the computer 8 outputs the reconstruction displays $D_i$ to the user 12 simultaneously by way of the display device 13.

Figure 7:
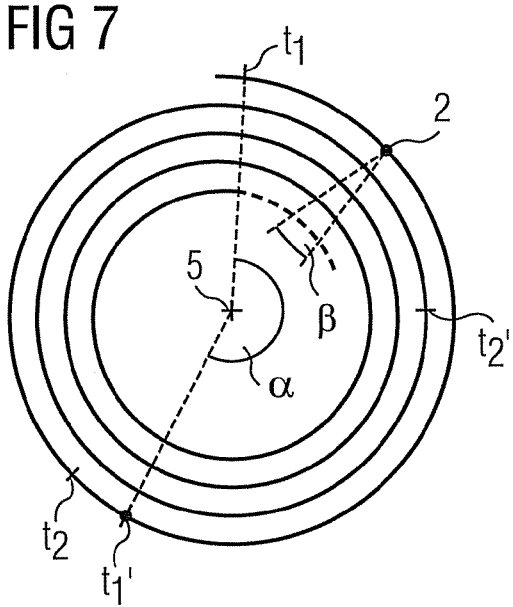
FIG. 7 to 9 show displacement operations of an x-ray source.
Figure 8:
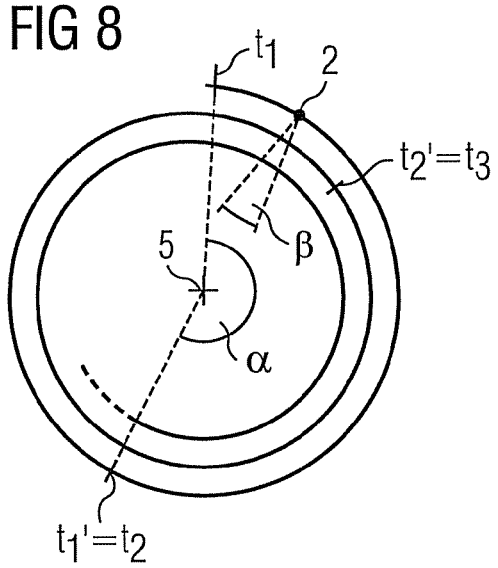
Figure 9:
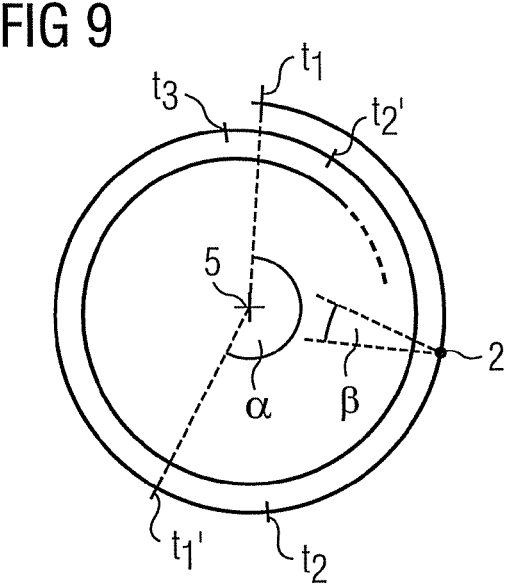

The x-ray system 1 used to capture the fluoroscopy images B can be a CT system for example. In this instance the recording arrangement 2 rotates continuously about the pivot axis 5. It therefore executes a number of complete circuits continuously about the pivot axis 5 according to the diagrams in FIG. 7 to FIG. 9. The circuits are shown here as spirals in FIG. 7 to 9, in order to be able to differentiate the individual circuits in FIG. 7 to 9 from one another. In reality the circuits are of course circular. Also only the path of the x-ray source 3 is shown in FIG. 7 to 9. At every time point the flat panel detector 4 lies diametrically opposite the x-ray source 3 relative to the pivot axis 5.

The group time periods are selected as required in FIG. 7 to 9. Generally they are selected to be as short as possible, to keep time-related reconstruction artifacts as small as possible. Generally the group time periods are the same for all the image groups $G_i$. They are generally selected so that the recording arrangement 2 (or the x-ray source 3) passes through a pivot angle α, which is 180° plus the fan angle β of the recording arrangement 2, relative to the pivot axis 5 during the group time period $\Delta t_i$. This procedure allows the so-called Feldkamp algorithm, which is generally known to those skilled in the art, to be used to determine the object reconstructions $R_i$. However it is possible and sometimes also expedient in individual instances to determine the pivot angle α differently. For example it is possible to select the pivot angle α to be smaller and only to carry out a so-called tomosynthesis.

Generally the user 12 will predetermine the pivot angle α, to be passed through by the recording arrangement 2 during the respective group time period, for the computer 8. In this instance the computer 8 uses the predetermined pivot angle α and the rotation speed of the recording arrangement 2 known to it to determine the corresponding group time periods automatically. In this instance in particular the group time periods for all the image groups $G_i$ are all identical to a setpoint time period $\Delta t$.

As mentioned above, the group intervals can likewise have the same value for all the image groups $G_i$, hereafter referred to as the temporal setpoint interval δt. The temporal setpoint interval δt here—see FIG. 7—can be longer than the setpoint time period $\Delta t$. The temporal setpoint interval δt can however also be identical to the setpoint time period $\Delta t$ according to FIG. 8. The temporal setpoint interval δt according to FIG. 9 can (again alternatively) be shorter than the setpoint time period $\Delta t$. The temporal setpoint interval δt should however be at least as long as half the setpoint time period $\Delta t$.

It is possible for the temporal setpoint interval δt to be permanently predetermined for the computer 8. It is likewise possible for the computer 8 to determine the temporal setpoint interval δt automatically based on the setpoint time period $\Delta t$. Again alternatively according to FIG. 10 it is possible for the computer 8 to receive the temporal setpoint interval δt from the user 12. In this instance a step S31 is inserted between the steps S1 and S2 according to FIG. 10. In step S31 the computer 8 receives the temporal setpoint interval δt from the user 12.

Figure 10:
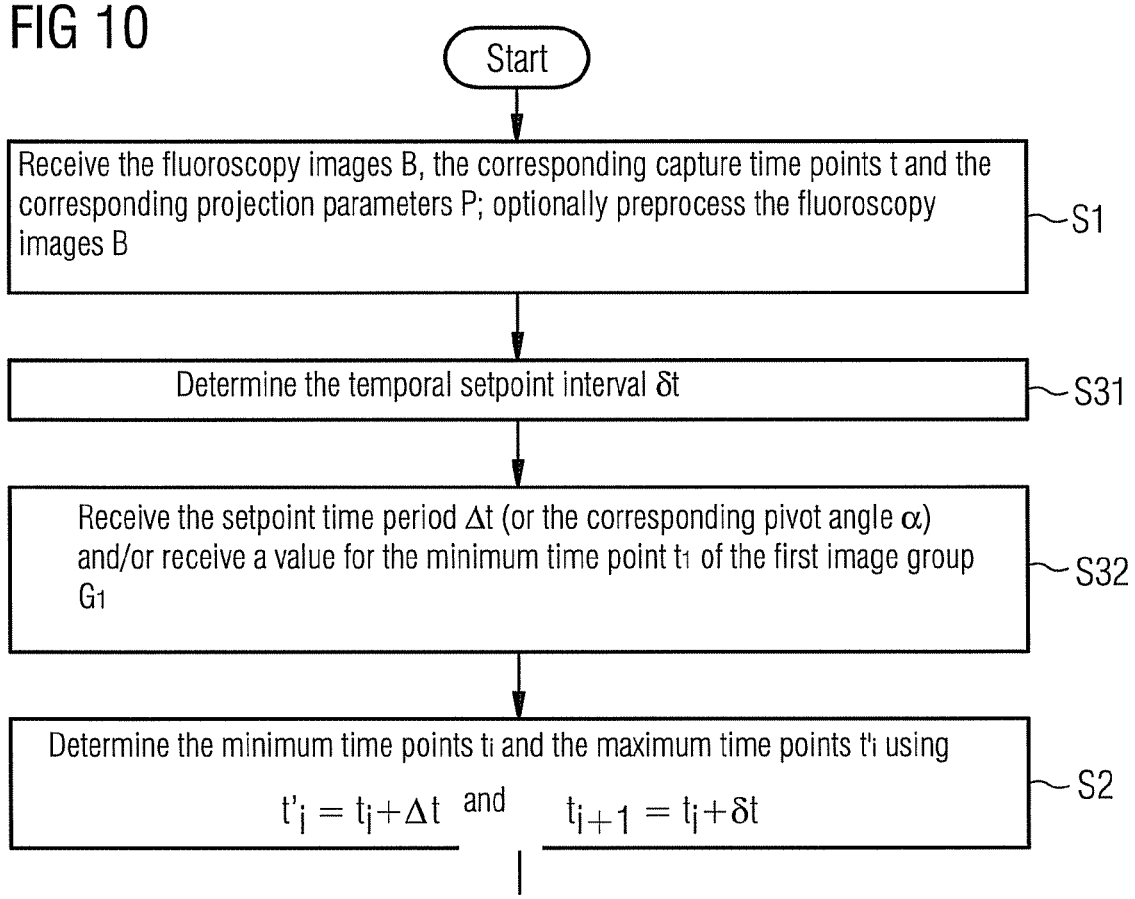
FIGS. 10 and 11 show flow diagrams.

Additionally according to FIG. 10 a step S32 can also be present. If step S32 is present, the computer 8 can receive the setpoint time period $\Delta t$ or the corresponding pivot angle α in step S32. As an alternative or in addition to predetermination of the setpoint time period $\Delta t$ or the corresponding pivot angle α, it is possible for the computer 8 to receive a value for the minimum time point $t_1$ of the first image group $G_1$ in the context of step S32.

According to FIG. 10 step S2 is also modified compared with the procedure in FIG. 2. In the context of step S2 in FIG. 10 the computer 8 determines the minimum time points $t_i$ and the maximum time points $t'_i$ according to the equations $$t'_i = t_i + \Delta t$$

$$t_{i+1} = t_i + \delta t.$$

If the examination object 7 does not move while the fluoroscopy images B are being captured, excellent results can be achieved with the procedures described above. If however the examination object 7 moves while the fluoroscopy images B are being captured, it is possible for motion-induced artifacts to occur to a significant extent. In this instance the procedure in FIG. 2 is preferably modified according to FIG. 11. The procedure in FIG. 11 is possible here as an alternative or in addition to the procedure in FIG. 10.

Figure 11:
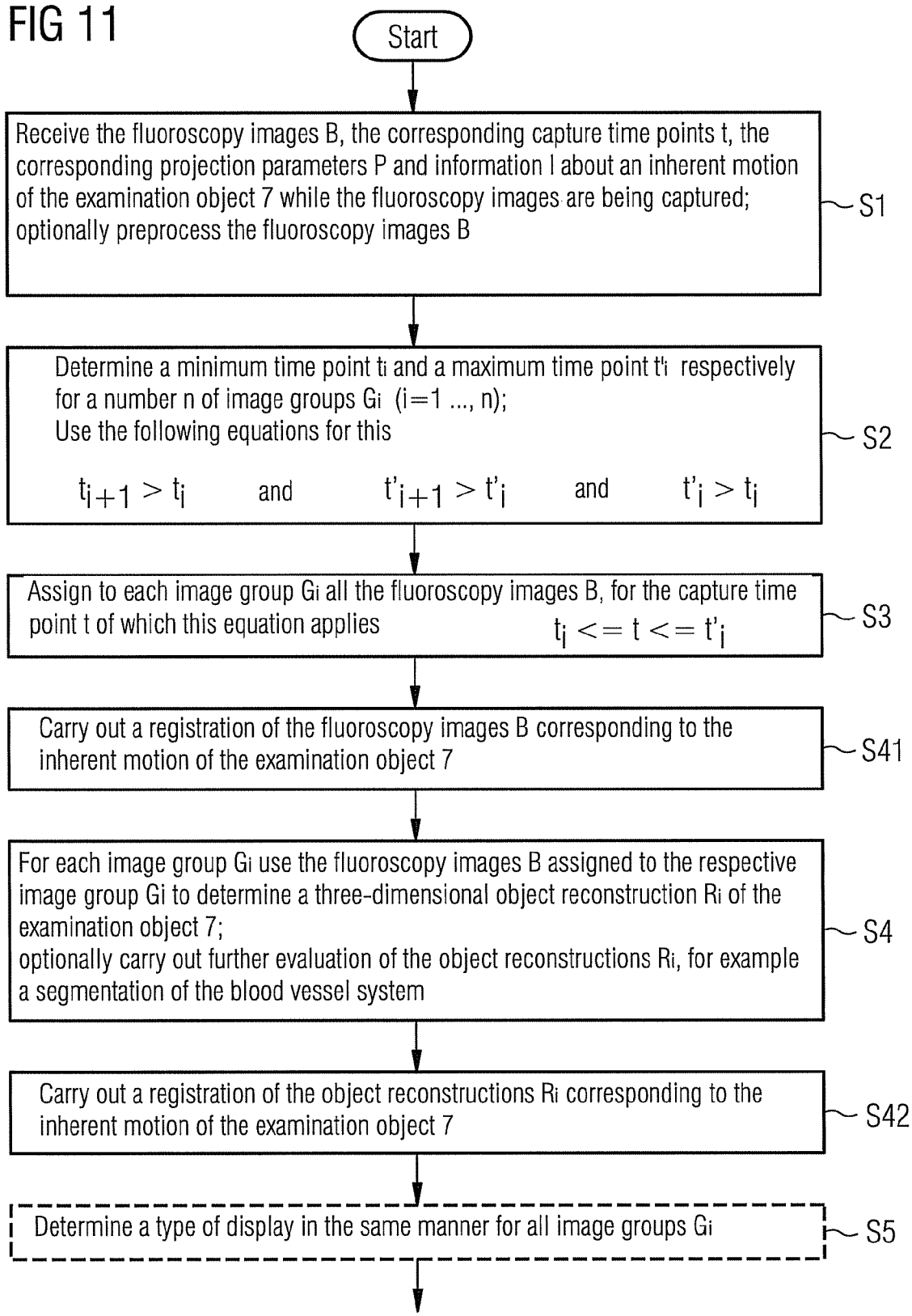

According to FIG. 11 step S1 in FIG. 2 is modified in such a manner that in addition to the fluoroscopy images B the computer 8 also receives information I about an inherent motion of the examination object 7 while the fluoroscopy images B are being captured. For example, if the examination object 7 corresponds to the human abdomen or pulmonary chamber, a chest strap may be used to capture a respiratory state of the examination object 7 and transmit it to the computer 8.

According to FIG. 11 a step S41 can be assigned in front of step S4 in FIG. 2. In step S41 the computer 8 carries out registration of the fluoroscopy images B. Registration of the fluoroscopy images B naturally corresponds here to the inherent motion of the examination object 7. Registration in step S41 can be rigid or elastic. The corresponding registration methods are known to those skilled in the art. They are as such not the subject matter of the present invention.

As an alternative or in addition to step S41 a step S42 can be assigned after step S4. In step S42 the computer 8 carries out registration of the object reconstructions $R_i$. Registration of the object reconstructions $R_i$ naturally also corresponds to the inherent motion of the examination object 7. Registration in step S42 can—as with registration in step S41—alternatively be rigid or elastic. The corresponding registration methods are also known to those skilled in the art in respect of step S42. They are as such not the subject matter of the present invention.

The present invention has been described above in conjunction with fluoroscopy images B, with the fluoroscopy images B being captured using an x-ray system 1, which is configured as a CT system. However the present invention can also be used if the fluoroscopy images B are captured by means of a differently configured x-ray system 1, for example a C-arm x-ray system.

Figure 12:
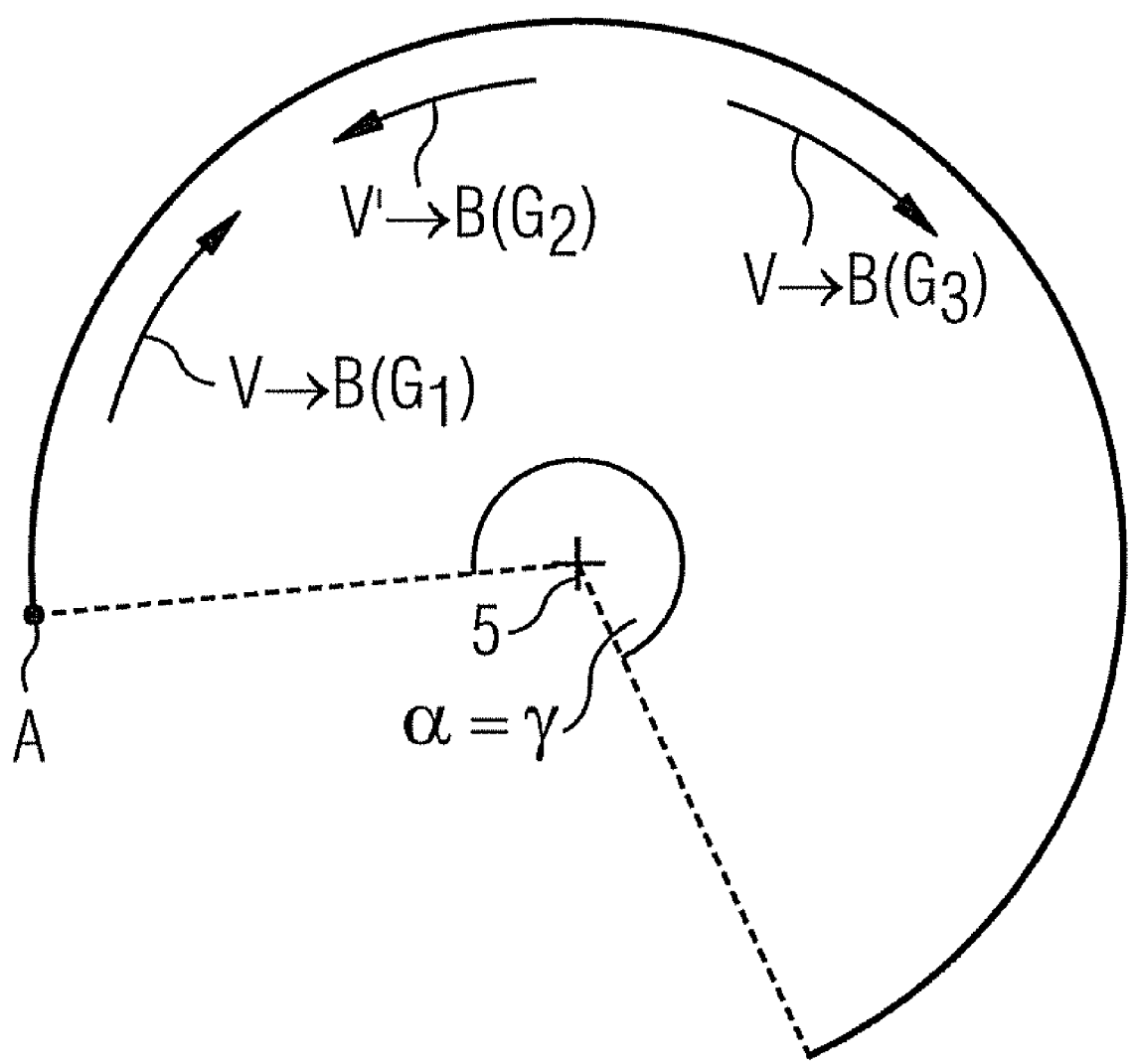
FIG. 12 shows a displacement operation of an x-ray source.

If the recording arrangement 2 of the differently configured x-ray system 1 is able, in a similar manner to a CT system, to execute a number of complete circuits about the pivot axis 5, this is immediately evident without further ado. However the present invention can also be applied, if the x-ray source 3 and flat panel detector 3 can only be pivoted over an overall angle γ of maximum 360°, for example 270° or 220° or 200°, according to FIG. 12. The recording arrangement 2 must then be pivoted back to its original position A after every forward displacement operation V by means of a backward displacement operation V'. The fluoroscopy images B are captured here at least during the forward displacement operations V. Alternatively fluoroscopy images B can be captured or not captured during the backward displacement operations V'. Generally all the fluoroscopy images B captured during a single displacement operation V, V' form an image group $G_i$. This is shown schematically in FIG. 12 for three displacement operations V, V'. The number ("three") of displacement operations V, V' shown here is of course purely exemplary.

The present invention has many advantages. In particular intuitive assignment of the blood flow to time is possible. A diagnosis based on the assignment of blood flow to time is therefore facilitated for the user (physician) 12.

The above description serves exclusively to describe the present invention. The scope of protection of the present invention should however be defined exclusively by the accompanying claims.

The invention claimed is:

1. An evaluation method for a plurality of two-dimensional fluoroscopy images of an examination object, comprising:
    receiving the fluoroscopy images captured at capture time points by a computer;
    assigning the capture time points to the fluoroscopy images;
    combining the fluoroscopy images into image groups;
    determining minimum time points and maximum time points to the image groups;
    assigning the fluoroscopy images to the image groups with the capture time points between the minimum time points and the maximum time points, wherein when the image groups are sorted by ascending the minimum time points, the corresponding maximum time points form a strictly monotonously ascending order;
    determining three-dimensional object reconstructions for the image groups based on the fluoroscopy images assigned to the image groups;
    determining two-dimensional reconstruction displays based on the three-dimensional object reconstructions; and
    outputting the two-dimensional reconstruction displays in codings to a user.

2. The evaluation method as claimed in claim 1, wherein the codings are colors or fill structures assigned to the image groups.

3. The evaluation method as claimed in claim 1, wherein the computer outputs the two-dimensional reconstruction displays simultaneously or as a temporal sequence.

4. The evaluation method as claimed in claim 3, wherein the computer outputs a part of each of the two-dimensional reconstruction displays which corresponds to none of preceding reconstruction displays in the temporal sequence.

5. The evaluation method as claimed in claim 1, wherein the computer receives information about an inherent motion of the examination object while the fluoroscopy images are captured and registers the fluoroscopy images corresponding to the inherent motion before or after determining the three-dimensional object reconstructions.

6. The evaluation method as claimed in claim 1, wherein directly consecutive minimum time points comprise a uniform temporal setpoint interval for all the image groups and a difference between a respective maximum time point and a respective minimum time point for each of the image groups is identical to a setpoint time period for all the image groups.

7. The evaluation method as claimed in claim 6, wherein the uniform temporal setpoint interval is at least as long as half of the setpoint time period.

8. The evaluation method as claimed in claim 6, wherein the computer receives the uniform temporal setpoint interval from the user.

9. The evaluation method as claimed in claim 1, wherein the minimum time points and the maximum time points are defined so that the fluoroscopy images assigned to the image groups can be used to determine the three-dimensional object reconstructions.

10. A computer program executable by a computer for evaluating a plurality of two-dimensional fluoroscopy images of an examination object, comprising:
    a computer subroutine that executes an evaluation method by:
        receiving the fluoroscopy images captured at capture time points;
        assigning the capture time points to the fluoroscopy images;
        combining the fluoroscopy images into image groups;
        determining minimum time points and maximum time points to the image groups;
        assigning the fluoroscopy images to the image groups with the capture time points between the minimum time points and the maximum time points, wherein when the image groups are sorted by ascending the minimum time points, the corresponding maximum time points form a strictly monotonously ascending order;
        determining three-dimensional object reconstructions for the image groups based on the fluoroscopy images assigned to the image groups;
        determining two-dimensional reconstruction displays based on the three-dimensional object reconstructions; and
        outputting the two-dimensional reconstruction displays in codings to a user.

11. A computer for evaluating a plurality of two-dimensional fluoroscopy images of an examination object, comprising:
    a processer that that executes an evaluation method by:
        receiving the fluoroscopy images captured at capture time points;
        assigning the capture time points to the fluoroscopy images;
        combining the fluoroscopy images into image groups;
        determining minimum time points and maximum time points to the image groups;
        assigning the fluoroscopy images to the image groups with the capture time points between the minimum time points and the maximum time points, wherein when the image groups are sorted by ascending the minimum time points, the corresponding maximum time points form a strictly monotonously ascending order;
        determining three-dimensional object reconstructions for the image groups based on the fluoroscopy images assigned to the image groups;
        determining two-dimensional reconstruction displays based on the three-dimensional object reconstructions; and
        outputting the two-dimensional reconstruction displays in codings to a user.

* * * * *